United States Patent [19]
Satherley et al.

[11] Patent Number: 6,141,574
[45] Date of Patent: Oct. 31, 2000

[54] AMBULATORY RECORDER HAVING SLIDING PERIOD SWITCHES

[75] Inventors: Richard J. Satherley, Felbridge, United Kingdom; Malcolm G. S. Williams, Stockholm; Alain Minoz, Bromma, both of Sweden

[73] Assignee: Medtronic, Inc., Minneapolis, Minn.

[21] Appl. No.: 09/129,920

[22] Filed: Aug. 6, 1998

[51] Int. Cl.[7] .......................... A61B 5/00; A61B 5/0432
[52] U.S. Cl. ..................... 600/361; 600/300; 600/508; 128/921
[58] Field of Search .................... 600/300, 301, 600/309, 361, 508, 509; 128/903, 920, 921

[56] References Cited

U.S. PATENT DOCUMENTS

| | | |
|---|---|---|
| D. 396,037 | 7/1998 | Cappa et al. . |
| 3,898,984 | 8/1975 | Mandel et al. . |
| 3,941,137 | 3/1976 | Vredenbregt et al. . |
| 4,003,379 | 1/1977 | Ellinwood, Jr. . |
| 4,082,084 | 4/1978 | Lipscher . |
| 4,129,125 | 12/1978 | Lester et al. . |
| 4,183,354 | 1/1980 | Sibley et al. . |
| 4,198,963 | 4/1980 | Barkalow et al. . |
| 4,333,475 | 6/1982 | Moreno et al. . |
| 4,353,375 | 10/1982 | Colburn et al. . |
| 4,365,636 | 12/1982 | Barker . |
| 4,370,983 | 2/1983 | Lichtenstein . |
| 4,464,172 | 8/1984 | Lichtenstein . |
| 4,503,859 | 3/1985 | Petty et al. . |
| 4,529,401 | 7/1985 | Leslie et al. . |
| 4,531,527 | 7/1985 | Reinhold, Jr. et al. . |
| 4,592,018 | 5/1986 | Wiegman . |
| 4,628,928 | 12/1986 | Lowell . |
| 4,632,119 | 12/1986 | Reichstein . |
| 4,667,682 | 5/1987 | Ihlenfeld, III . |
| 4,684,367 | 8/1987 | Schaffer et al. . |
| 4,715,385 | 12/1987 | Cudahy et al. . |
| 4,748,562 | 5/1988 | Miller et al. . |
| 4,771,772 | 9/1988 | DeWitt . |
| 4,774,956 | 10/1988 | Kruse et al. . |
| 4,794,934 | 1/1989 | Motoyama et al. . |
| 4,895,161 | 1/1990 | Cudahy et al. . |
| 4,900,305 | 2/1990 | Smith et al. . |
| 4,917,092 | 4/1990 | Todd et al. . |
| 4,974,599 | 12/1990 | Suzuki . |
| 5,002,062 | 3/1991 | Suzuki . |
| 5,007,427 | 4/1991 | Suzuki et al. . |
| 5,010,888 | 4/1991 | Jadvar et al. . |
| 5,012,411 | 4/1991 | Policastro et al. . |
| 5,016,636 | 5/1991 | Kulakowski . |
| 5,042,481 | 8/1991 | Suziki et al. . |
| 5,072,458 | 12/1991 | Suzuki . |
| 5,086,778 | 2/1992 | Mueller et al. . |
| 5,107,835 | 4/1992 | Thomas . |
| 5,111,396 | 5/1992 | Mills et al. . |
| 5,111,818 | 5/1992 | Suzuki et al. . |
| 5,113,869 | 5/1992 | Nappholz et al. . |
| 5,117,827 | 6/1992 | Stuebe et al. . |

(List continued on next page.)

FOREIGN PATENT DOCUMENTS

0 356 603   9/1988   Sweden .

*Primary Examiner*—Eric F. Winakur
*Attorney, Agent, or Firm*—Thomas F. Woods; Michael J. Jaro; Harold Patton

[57] ABSTRACT

An ambulatory data recorder having a slidable patient activity period switch. The slidable patient activity period switch permits the patient to slide the switch from a first position to a second position upon the start of a pre-defined activity, e.g. eating. Upon completion of the pre-defined activity, the switch is slide from the second position back to the first position. While in either the first or second position the switch position corresponds to a marking on the recorder enclosure such that the patient can readily understand which activity the switch is indicating. The slidable patient activity period switch is further configured to have minimal power consumption. In one embodiment the switch is provided through a standard keyboard interrupt service routine.

38 Claims, 6 Drawing Sheets

U.S. PATENT DOCUMENTS

| | | |
|---|---|---|
| 5,131,816 | 7/1992 | Brown et al. . |
| 5,158,083 | 10/1992 | Sacristan et al. . |
| 5,188,104 | 2/1993 | Wernicke et al. . |
| 5,213,568 | 5/1993 | Lattin et al. . |
| 5,222,503 | 6/1993 | Ives et al. . |
| 5,224,485 | 7/1993 | Powers et al. . |
| 5,226,431 | 7/1993 | Bible et al. . |
| 5,228,450 | 7/1993 | Sellers . |
| 5,238,001 | 8/1993 | Gallant et al. . |
| 5,261,401 | 11/1993 | Baker et al. . |
| 5,263,491 | 11/1993 | Thornton . |
| 5,273,033 | 12/1993 | Hoffman . |
| 5,292,344 | 3/1994 | Douglas . |
| 5,305,202 | 4/1994 | Gallant et al. . |
| 5,305,761 | 4/1994 | Byrne et al. . |
| 5,307,263 | 4/1994 | Brown . |
| 5,309,920 | 5/1994 | Gallant et al. . |
| 5,338,157 | 8/1994 | Blomquist . |
| 5,341,291 | 8/1994 | Roizen et al. . |
| 5,343,870 | 9/1994 | Gallant et al. . |
| 5,355,892 | 10/1994 | Saltzstein . |
| 5,368,562 | 11/1994 | Blomquist et al. . |
| 5,381,351 | 1/1995 | Kwong et al. . |
| 5,388,587 | 2/1995 | Knutsson et al. . |
| 5,411,022 | 5/1995 | McCue et al. . |
| 5,429,602 | 7/1995 | Hauser . |
| 5,431,634 | 7/1995 | Brown . |
| 5,432,698 | 7/1995 | Fujita . |
| 5,438,985 | 8/1995 | Essen-Moller . |
| 5,479,019 | 12/1995 | Gross . |
| 5,479,935 | 1/1996 | Essen-Moller . |
| 5,507,904 | 4/1996 | Fisher et al. . |
| 5,526,809 | 6/1996 | Fiddian-Green . |
| 5,545,183 | 8/1996 | Altman . |
| 5,607,460 | 3/1997 | Kroll . |
| 5,645,068 | 7/1997 | Mezack et al. . |
| 5,657,759 | 8/1997 | Essen-Moller . |
| 5,701,894 | 12/1997 | Cherry et al. . |
| 5,704,368 | 1/1998 | Asano et al. . |
| 5,704,890 | 1/1998 | Bliss et al. . |
| 5,749,907 | 5/1998 | Mann . |

States list:

|  | T0 | T1 | T2 | T3 | T4 | T5 | T6 |
|---|---|---|---|---|---|---|---|
| A | 1 | 1 | 0 | 0 | 1 | 1 | 1 |
| B | 0 | 0 | 1 | 1 | 0 | 0 | 0 |
| C | 0 | 0 | 0 | 0 | 0 | 0 | 0 |
| D | 1 | 0 | 1 | 0 | 1 | 1 | 1 |
| E | 1 | 1 | 1 | 1 | 1 | 0 | 1 |
| Interrupt | 0 | 1 | 0 | 1 | 0 | 1 | 0 |

FIGURE 8C

AMBULATORY RECORDER HAVING SLIDING PERIOD SWITCHES

FIELD OF THE INVENTION

The present invention relates to a method for ambulatory recording, for medical and especially for diagnostic purposes, by means of a portable recorder slidable patient activity period switches, switch permitting a notation to be made in the recorded data upon the start of a pre-defined activity, e.g. smoking.

Ambulatory recording and recorders are widely used. Such devices include the Digitrapper Mk III™ ambulatory recorder from Synectics Medical AB, the GastroScan II™ from Medical Instruments Corporation, and the SuperLogger™ from Sandhill Scientific. These types of devices make it possible for patients to remain at home, or at the least be ambulant in a hospital setting while physiological data is recorded. Typically the devices comprise a lightweight recorder in which the desired physiological data signals are temporarily stored and later downloaded for future analysis.

Many types of physiological data may be recorded, including ECG (Electrocardiogram), EEG (Electroencephalogram) or pH and pressure (Motility) in the gastrointestinal tract. Preferably such a recorder should be able to record among a programmable number of channels at a variety of programmable frequencies.

One problem often faced with designing ambulatory recorders lies in the fact that ambulatory medical recorders record data over a prolonged period of time, e.g. 24 hours. During the recording of data it is often important to have information regarding the times of the patient's activity. Activities of interest include meal time and the times during which the patient is eating or sleeping.

Past ambulatory medical devices have permitted the patient to note in the data as it is being collected whether such activities of interest have occurred and when. In past devices, such as the Digitrapper™ of Synectics Medical AB, Stockholm, Sweden, a push button was used to note the activities. That is, when mealtime occurred, for example, the patient depressed the button to note a meal began. When the meal ended the patient again pushed the button.

A problem with the push button activity notation, however, is that the patient could forget or lose track of which state the button is in. For example, while smoking, the patient could press the button upon the first cigarette, and not remember to depress after the cigarette ended. In addition, the patient could press it twice after the cigarette ended, which would actually then not a second cigarette was begin. Over the course of a twenty four hour recording session, such mistakes have proven all too easy to make.

Thus there is a need for an ambulatory medical device which positively reports the period switch position in a manner clearly noticeable by the patient.

There is a further need for such a recorder which, because the recorder is battery operated, is able to report such switch position in a manner which minimizes energy usage.

There is a still further need for such a recorder which, because its complexity should be minimized, provides such a switch through a software-based scheme.

SUMMARY OF THE INVENTION

An ambulatory data recorder having a slidable patient activity period switch. The slidable patient activity period switch permits the patient to slide the switch from a first position to a second position upon the start of a pre-defined activity, e.g. eating. Upon completion of the pre-defined activity, the switch is slide from the second position back to the first position. While in either the first or second position the switch position corresponds to a marking on the recorder enclosure such that the patient can readily understand which activity the switch is indicating. The slidable patient activity period switch is further configured to have minimal power consumption. In one embodiment the switch is provided through a standard keyboard interrupt service routine.

BRIEF DESCRIPTION OF THE DRAWINGS

The FIGS. are not necessarily to scale.

DETAILED DESCRIPTION OF THE DRAWINGS

Figure 1A:
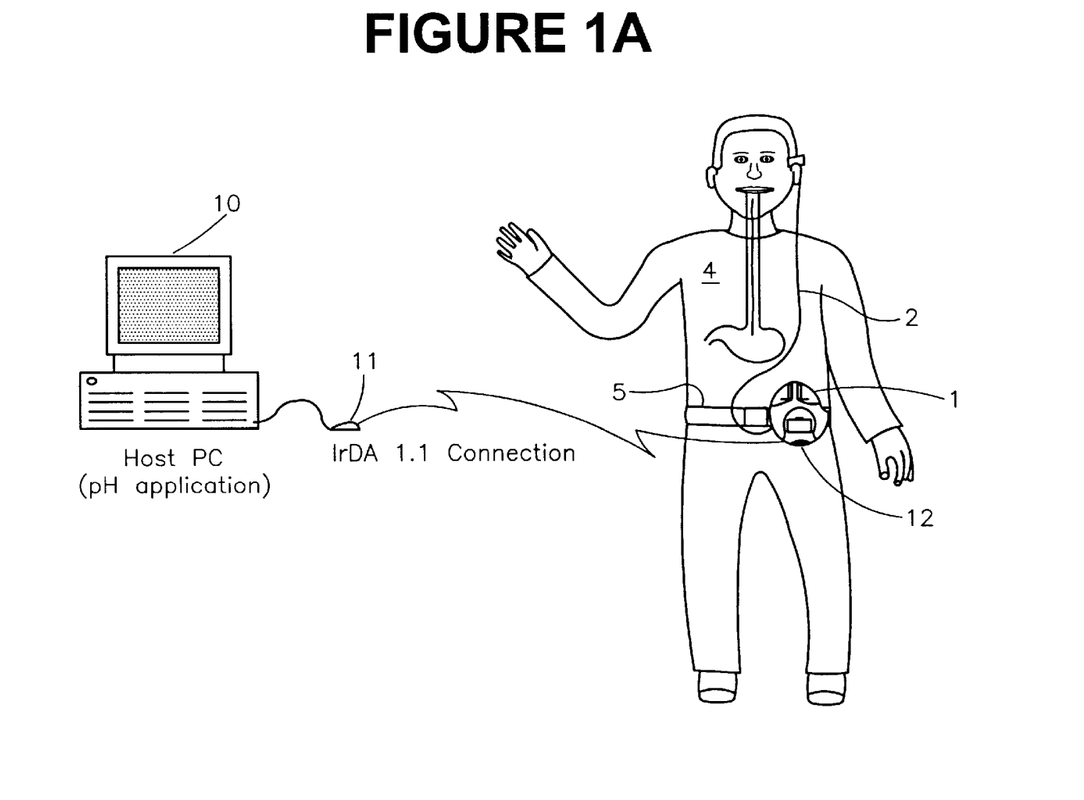
FIG. 1A depicts an ambulatory recorder of the present invention.

FIG. 1A depicts an ambulatory recorder of the present invention. As seen, ambulatory recorder 1 of the present invention may be carried by a patient. In the preferred embodiment, the recorder may be either carried through a mounting in the back of the recorder enclosure which fastens to a patient's belt 5, or the same mounting may be coupled to be carried using a shoulder harness (not shown). As seen, recorder is coupled to the patient 4 through one or more sensing catheters 2. Sensing catheters may be positioned in any area of the patient's body, from which data is to be sensed, including the esophagus, as depicted in this FIG. It should be noted, the ambulatory recorder of the present invention may be used to collect many or various types of data including gastrointestinal (including pH and pressure), neurological, as well as neuromuscular, EEG or EMG data.

Among the various sensing catheters which may be coupled to the device are manometry catheters and pH testing catheters, including the Synectics Medical AB, Stockholm, Sweden Model G 91-9 series of Multi use pH catheters; Synectics Medical AB Model G 91-2 series of Multi use pH catheters with perfusion port; or the Zinectics Inc., Salt Lake City, Utah disposable 24 pH catheter Model series G91-6 or G 91-7. While a single catheter 2 is shown depicted in this figure, recorder further permits two separate sensors to be coupled to the device, as seen in FIG. 1B.

As further seen in this figure, the recorder may also communicate with a host PC 10 via an infra red data link facility through an IrDA connection 11, for example, a JETEYE ESI-57680 available form Extended Systems, Inc., Boise, Id., which connects with the recorder using the infra Red Data Association 1.1 Connection Protocol. As seen, infra red data connection makes a link to infra red port 12 on recorder.

Figure 1B:
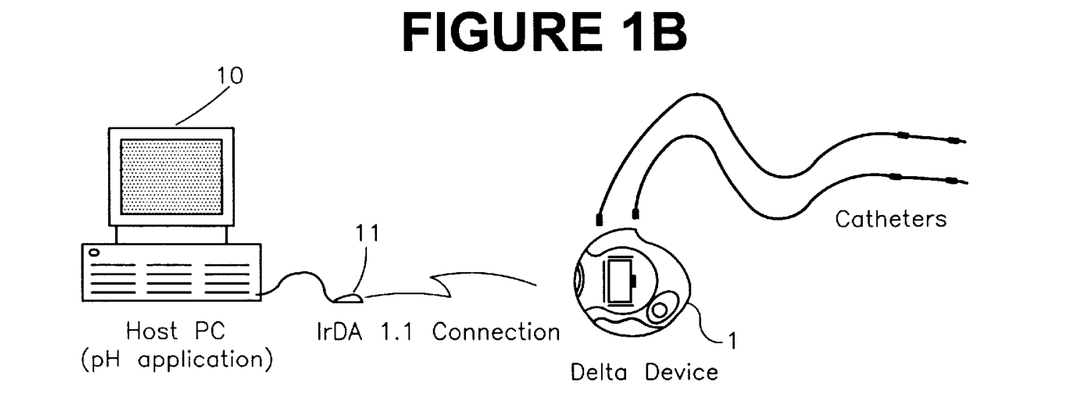
FIG. 1B illustrates a further manner in which the recorder 1 may also have an infra red data communication link made with a host PC.

FIG. 1B illustrates a further manner in which the recorder 1 may also have an infra red data communication link made with a host PC. In particular, the infra red data communication data recorder may be further made when the recorder is not worn by the patient. As discussed in more detail below, one of the advantages of the present invention is that the infra red data components and recorder case permits such a link to be made when the device is worn as shown in FIG. 1A as well as if the device is merely removed from the patient and positioned in proximity to mouse 11.

Figure 2:
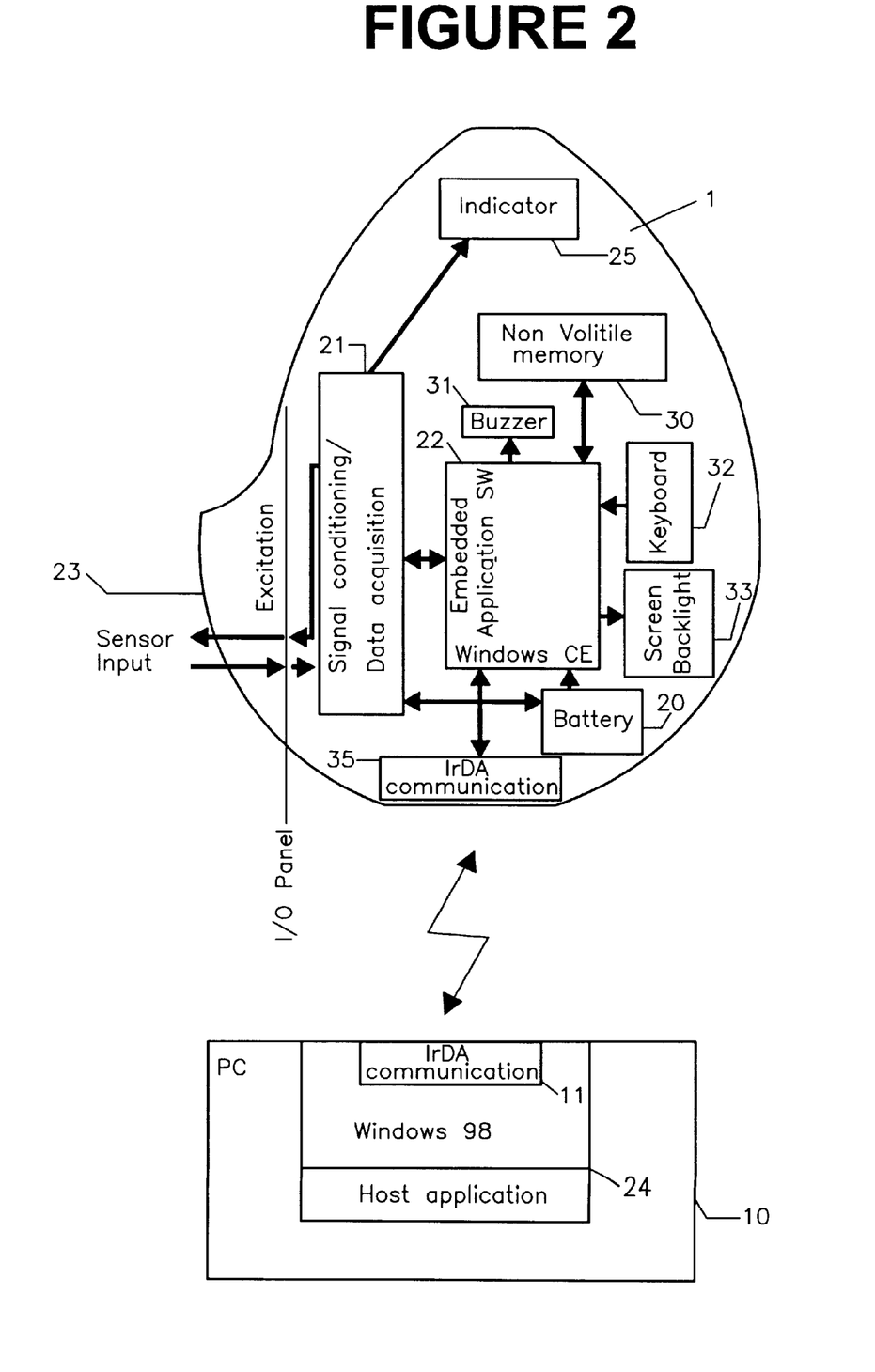
FIG. 2 is a block diagram of the data recording system shown in FIG. 1B.

FIG. 2 is a block diagram of the data recording system shown in FIG. 1B. As seen, recorder 1 features a battery 20 which is coupled to the signal conditioning /data acquisition block that is driven by a real time processor 21, the battery is coupled as well as to a non-real time processor 22 that runs the application. As disclosed in more detail below, real time processor 21 is a lower power processor which is used to sample data which is received from sensor input 23 by a sensor attached thereto (not shown in this FIG.).

Sampling is achieved through the signal conditioning providing an excitation to the sensor coupled to sensor input 23. Such excitation voltage is often used to power and, thus, permit sensing to occur in a variety of different types of sensors, including pressure sensors, as is well known in the art. The sampling and sensing controls are provided by the real time processor 21. Real time processor also drives a LED indicator 25 to show the system is running even when the screen is off.

As further seen, this processor is coupled to second non-real time processor 22. Second processor 22 is provided primarily to perform those high processing operations associated with multitasking, graphical user interface, floating point calculation, Infra Red communication and long term memory storage. In particular, second processor is primarily provided to operate a Windows CE operating system as well as one or more embedded applications, as depicted. As further seen, this processor is coupled to audible buzzer 31 as well as keyboard controls 32, a screen 33 and non-volatile memory 30. Non-volatile memory provides a long term memory for the device such that data can be recorded and preserved even if power is lost. In the preferred embodiment, keyboard controls processes a series of four push buttons, each of which provide one or more different types of system inputs, as provided by the Windows CE™ operating system, available from Microsoft Corporation, Redmond, Wash.

As further seen in this figure, recorder features an infra red port 35 to communicate with the host PC. As depicted in FIG. 1B, the infra red connection permits the recorder 1 to receive and exchange data with host PC 10. Host PC, as seen, includes both a Windows 98™ operating system available from Microsoft Corporation, Redmond, Wash., as well as one or more host applications. Host applications permit the treatment of the recorded values and help for diagnostic.

In the preferred embodiment the real time processor is the model PIC16LC67 from Microchip Technology Inc., Chandler, Ariz.; the non real time processor is the model ElanSC400 from Advanced Micro Devices, Inc. Sunnyvale, Calif.; and non-volatile memory is the model Minicard AMMCL004AWP from Advanced Micro Devices, Inc. Sunnyvale, Calif.

Figure 3:
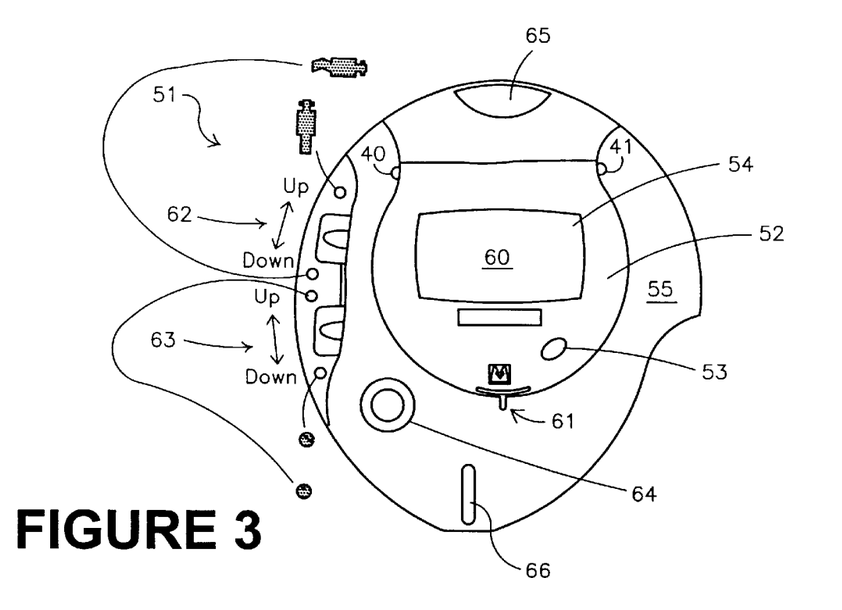
FIG. 3 is a front view of recorder according to the present invention.

FIG. 3 is a front view of recorder according to the present invention. In this view, recorder 51 has its movable front cover 52 closed. As discussed in more detail below, front cover further includes a movable push button shield 53 which allows access to one of the push button controls covered by the cover while in the down position. Shield, although allowing access to push button, obscures any notation of push button from the viewer when the cover is closed such that a very simplified control interface is presented to any user when the cover 52 is closed. Cover also features a transparent window 54 to permit viewing of the LCD screen 60 which is integral with recorder (further depicted in FIG. 2). As mentioned, cover may be moved from a closed position, shown in this figure, to an open position, shown in FIG. 4.

As seen, recorder also features a pair of period switches 62 and 63 which are movable in a linear fashion from a first to a second position. In the preferred embodiment, period switch 62 is a body position switch and the up position is used to mark periods when the patient is lying down or in a supine position. The down position is used to mark periods when the patient is standing or sitting upright. Period switch 63 preferably is a meal switch and the up position is used to mark a meal period while the down position is used for periods when the patient is not eating. The device further features, in its design, an event button 64 which the patient presses to mark events. Such events may include heart palpitations or reflux. Clock button 53, period switches 62 and 63 and event button 64 are all coupled to the keyboard function 32, shown in FIG. 2. As discussed below, the a particular advantage of the slide switch design of the present invention is that it permits the standard keyboard interrupt service routines of the microprocessor 22 to be used, while still minimizing power usage.

As seen, the device further features an infra red data output port having a two plane infra red lens 65. This feature is coupled to the infra red communication block 35 depicted in FIG. 2 and permits the device to communicate, through an infra red connection, to a host PC. The device also features an operation indicator light 66 which would indicate device operation.

Figure 4:
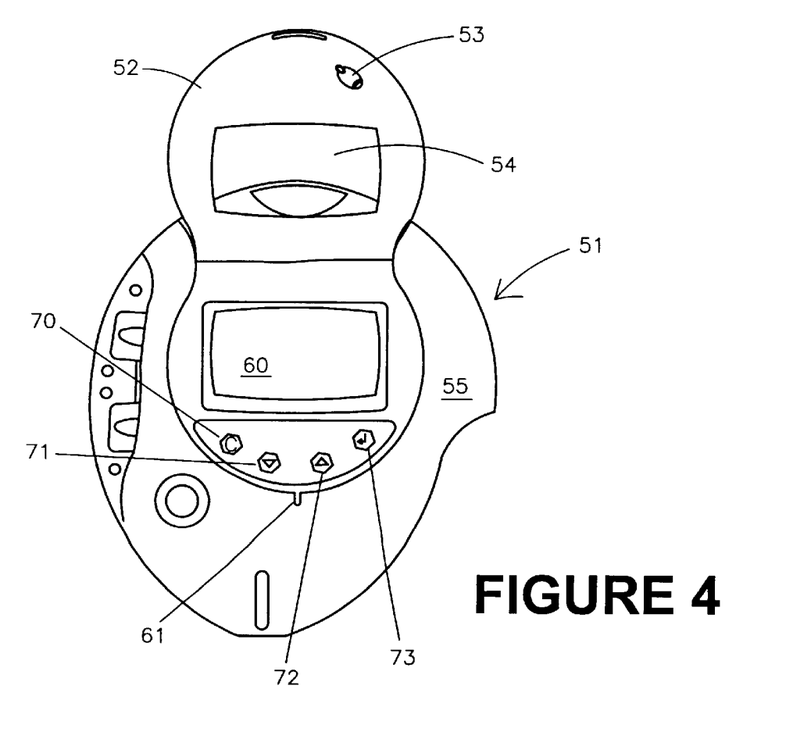
FIG. 4 is a front view of the recorder 51 in which the cover 52 has been raised and the device is open.

FIG. 4 is a front view of the recorder 51 in which the cover 52 has been raised and the device is open. As seen, when open, a series of controls 70, 71, 72 and 73 are exposed. As seen, control 70 is a push button and features, at its front face, the mark C. This control permits the user to return to the previous screen shown on display 60 without having to save any changes. Control 71 is a push button which, in the preferred embodiment, moves the selection bar shown in 60 to the next item down. Control 72 is a push button which, in the preferred embodiment, moves the selection bar to the next item up. Control 73 is, preferably, a push button which executes the current selection in the preferred embodiment.

As seen by a comparison of FIG. 3 and FIG. 4, control push button 73 may be operated regardless of whether the cover is opened or closed during the provision of movable push button 53. An important feature of this shield, however, is that it presents a different notation for the push button when the cover is closed as compared to when the cover is open. As discussed above, past ambulatory recorders have performed less than satisfactorily because too many controls were presented to the patient. While such controls are necessary to be presented to the physician so that the device may be programmed and its operating parameters set in an acceptable manner, such controls are not necessary for the patient when the device is merely recording. Thus, the movable push button shield, mounted to the movable cover, permits the device to provide an enhanced control feature set to a physician while limiting the control feature set for the patient. Cover movement is further controlled by the open cover catch 61 which permits the cover to only be open through a tool, in the preferred embodiment a pen tip. Although not shown in this figure, another feature important to the device operation is that of the hinge point on which the cover is mounted. In the preferred embodiment hinge is functionally a break-away hinge such that if excessive force(e.g. greater than eight pounds) is provided to the cover when open it will release from its hinge points without breaking such that it may thereafter be reinserted into its hinge. The breakaway feature is provided in a known manner, a deformable polymer cover along with removable hinges, e.g. interlocking hemispherical hinge points and recesses.

Figure 5:
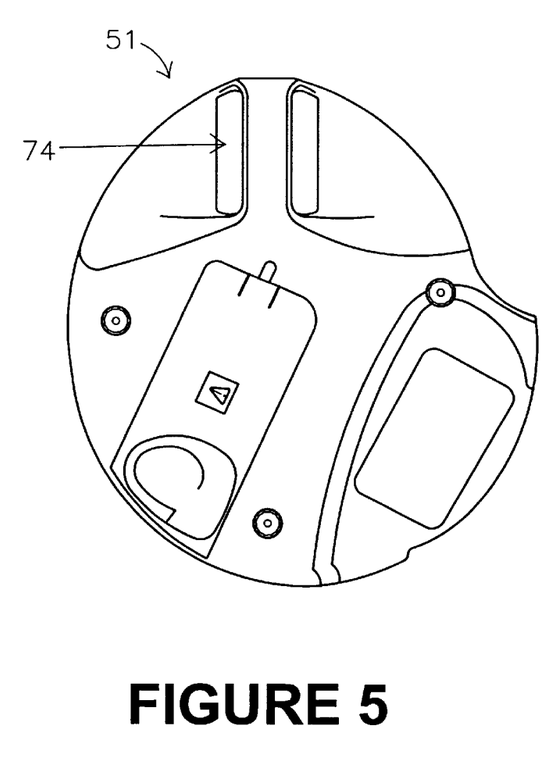
FIG. 5 is a back view of the recorder.

FIG. 5 is a back view of the recorder. As seen, recorder 51 features a belt loop 74 which may be used to mount the recorder to a patient using either the patient's belt or the shoulder strap.

Figure 6:
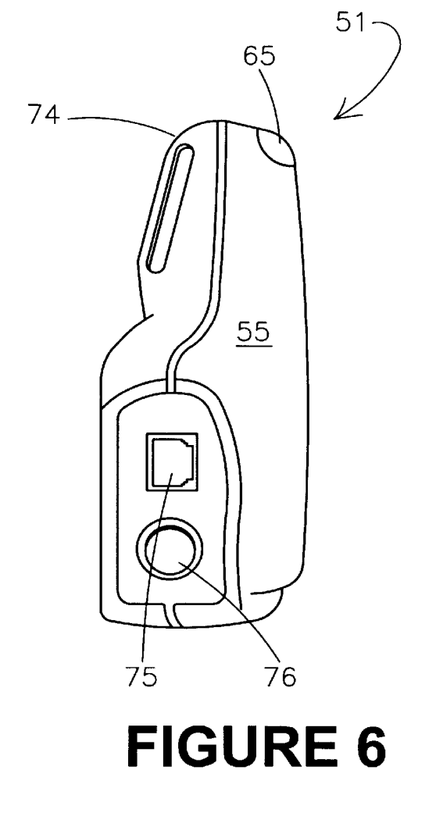
FIG. 6 is a side view of the recorder.

FIG. 6 is a side view of recorder 51. As further seen in this view, housing or enclosure 55 features a pair of sensor inputs 75 and 76. In the preferred embodiment, input 75 is for a pH catheter while input 76 is for a pressure measuring catheter. As further seen, recorder features an infra red lens 65 which permits an infrared link to a host be made using the IrD communication components shown in FIG. 2. As seen in this view lens is positioned along both an upper as well as a side surface of the recorder enclosure. This two sided or multi plane lens thereby permits a large degree of exposure to the internal IrD components inside the enclosure and thus permits an IrD link to be made with the recorder in a variety of positions, relative to the IrDA communication device 11 (referring to FIGS. 1A and 1B) Lens may be made of an known standard lens material. In the preferred embodiment lens is made of polycarbonate and enclosure itself, including cover, is fashioned from the polymer Crastin™ XMB 850 FR available from E. I. Du Pont De Nemours And Company, Wilmington, Del. The lens, however, should be formed so as to reach across both the upper side as well as front side of the recorder (referring once again to FIG. 6).

As discussed above, the recorder according to the present invention features a sliding patient activity period switch that positively reports the period switch position in a manner clearly noticeable by the patient. The switch further reports such switch position to the data recorder in a manner that minimizes energy usage. Finally, the switch of the present invention is basically software enabled, thus allowing simple mechanical construction.

Thus an ambulatory data recorder according to the present invention has a slidable patent activity period switch. The slidable patent activity period switch permits the patient to slide the switch from a first position to a second position upon the start of a pre-defined activity, e.g. smoking. Upon completion of the pre-defined activity, the switch is slide from the second position back to the first position. While in either the first or second position the switch position corresponds to a marking on the recorder enclosure such that the patient can readily understand which activity the switch is indicating. The slidable patent activity period switch is further configured to have minimal power consumption. In the preferred embodiment the switch is provided through a standard keyboard interrupt service routine.

Figure 7A:
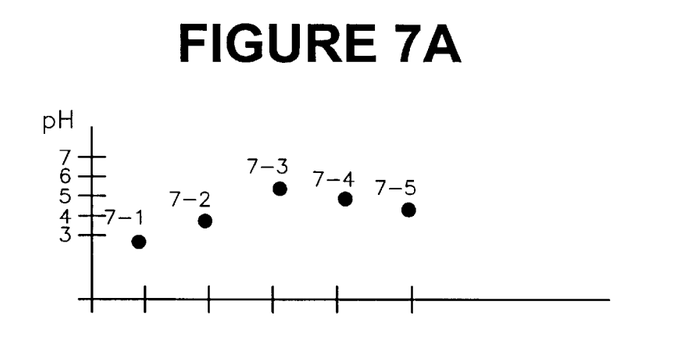
FIG. 7A illustrates the data collected by the recorder while the sliding period switch is an different positions.

FIG. 7A illustrates the data collected by the recorder while the sliding period switch is a different positions. This illustration features a pH value to be recorded and having patient position to be reported although it should be understood a collection of various parameters may be recorded, depending on the type of sensor couple to the recorder, as discussed above. Moreover, while patient position is shown reported here, other activity periods could also be used, such as smoking, eating, drinking exercising, etc., to name only a few. In the preferred embodiment the recorder has two switches, as illustrated above, which are used to indicate eating and sleeping (position.) As seen, the recorder records data as a series of discrete data points, 7-1 through 7-5. These correspond in this illustration to sensed values of pH, as seen at the left axis. The slide switches, moreover are preferably biased in either position. That is the slide switch is biased to the first position until moved to the second position, at which time the slide switch is biased in the second position, until moved to the first position. In such a manner the switch is less likely to be inadvertently moved.

Figure 7B:
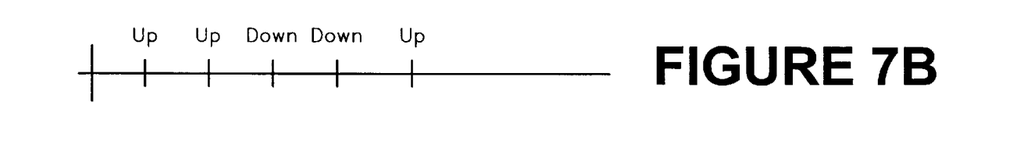
FIG. 7B illustrates the reported position of the slide switch in the data stream.
Figure 7C:
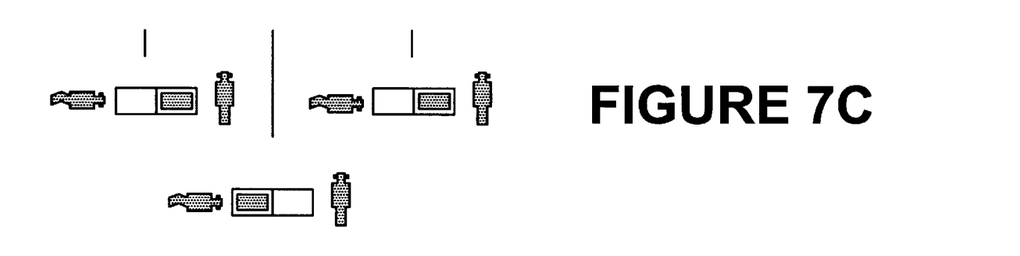
FIG. 7C illustrates the actual switch position as would be seen by the patient.

FIG. 7B illustrates the reported position of the slide switch in the data stream, and FIG. 7C illustrates the actual switch position as would be seen by the patient. Concurrent with the recording of the data points 7-1 through 7-5 illustrated in FIG. 7A, the device further records the position the slide switch is in and notes it in the data recording as seen in FIG. 7B. As illustrated switch position is noted as individual notations of switch position concurrent with the times of the recorded pH values (shown in FIG. 7A.) Switch position data, however, may be used, processed and displayed in any desired manner. The slide switch of the present invention merely provides the ability for this information to be collected, while further allowing the patient to readily determine the position of the switch and thus the period information being reported.

Figure 8A:
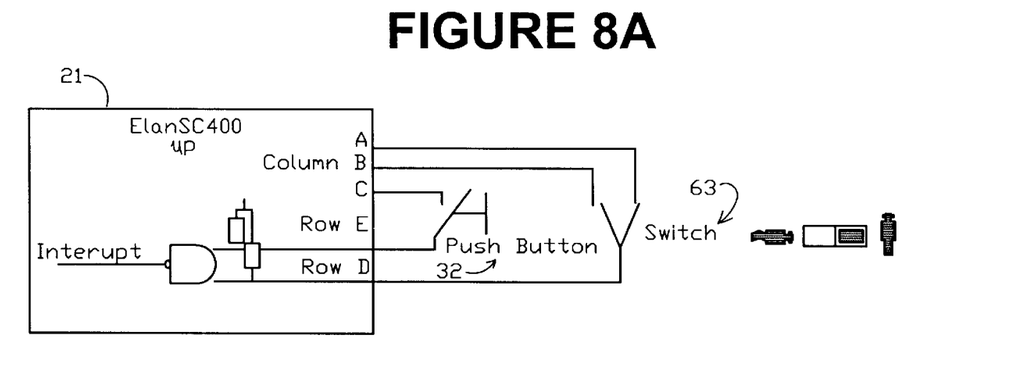
FIG. 8A is a schematic diagram of the associated circuitry used to service the sliding period switch.

FIG. 8A is a schematic diagram of the associated circuitry used to service the sliding period switch. The so-called column signals A,B,C are outputs and the so-called row signals D, E are inputs. Whenever one or more of the row goes to 0, it generates an interrupt. The purpose of the invention is to acquire the interrupt, read the position of the slide and go back to a sleep mode immediately to save power.

Figure 8B:
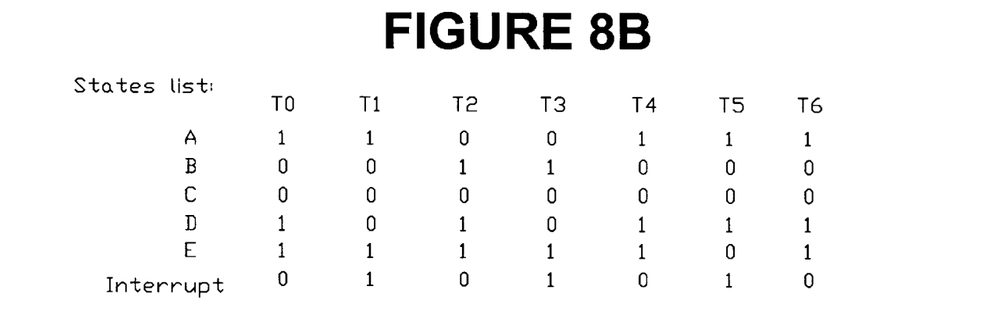
FIG. 8B depicts the state of the signal at different times.

FIG. 8B depicts the states of points A, B, C, D, E and the interrupt signal noted on FIG. 8A while the switch is different positions. These FIGS will now be explained together. At time T0, the slide switch is in UP position and no interrupt is serviced, the processor sleeps. At time T1, we move the slide switch to DOWN position, the row input D goes to 0, an interrupt is generated, the processor wakes up read the state of A and B. Since A=1 and B=0, it means that the switch moved to position DOWN, the application is notified as if a key was pressed. The interrupt service routine inverts then the outputs A,B (T2) to stop generating an interrupt and goes to sleep again.

At time T3, we move the slide switch to UP position, the row input D goes to 0, an interrupt is generated, the processor wakes up read the state of A and B. Since A=0 and B=1, it means that the switch moved to position UP, the application is notified as if a key was pressed. The interrupt service routine inverts then the outputs A,B (T4) to stop generating an interrupt and goes to sleep again.

We can compare the respond of the switch to the respond of a push button. At time T5, we press the push button, the row input E goes to 0, an interrupt is generated, the processor wakes up read the state of row E, the application is notified the key was pressed. The interrupt service routine ends when the push button is released (T5) and goes to sleep again.

Figure 8C:
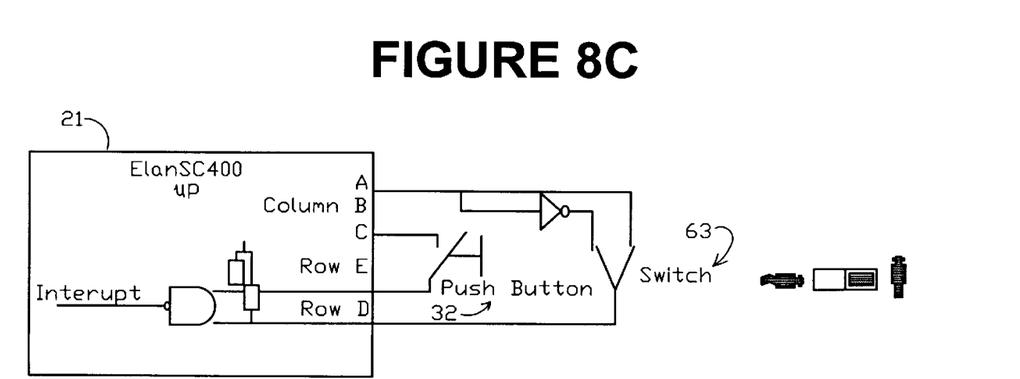
FIG. 8C shows another implementation of the circuitry.

Since the state of A and B are always inverted, we can implement the same concept with only one row using an inverter as seen in FIG. 8C.

In such a manner the recorder is able to have a slide switch to indicate a pre-defined patient activity period while minimizing energy usage and device complexity.

Although various embodiments of the invention have been disclosed, this is done for purposes of illustration and is not intended to be limiting with regard to the scope of the invention. It is contemplated various substitutions, alterations and/or modifications may be made to the disclosed embodiment without departing from the spirit and scope of the invention. Such modifications may include substituting elements or components which perform substantially the same function in substantially the same way to achieve substantially the same result for those described herein.

What is claimed is:

1. An ambulatory data recorder, comprising:
   a sensor to sense physiologic data;
   means for sampling and recording the sensed physiologic data; and
   a patient activated period slide switch, the slide switch being moveable from a first position, where a period start notation is made in the recorded data, to a second position, where a period end notation is made in the recorded data.

2. An ambulatory recorder according to claim 1, wherein the slide switch is biased to the first position until removed to the second position, at which time the slide switch is biased in the second position, until moved to the first position.

3. An ambulatory recorder according to claim 1, wherein the slide switch is slides in a linear manner.

4. An ambulatory recorder according to claim 1, wherein the means for sampling and recording the sensed physiologic data comprises a non real time processor.

5. An ambulatory recorder according to claim 4, wherein the processor further comprises keyboard interrupt service routines, the processor further having executable software to permit the slide switch movement to access a keyboard interrupt service routine in the means for sampling and recording the sensed physiologic data and thereby insert a period start notation in the recorded data when the slide switch is moved to the first position.

6. The ambulatory data recorder according to claim 1, wherein the means for sampling and recording the sensed physiologic data further comprises a non-volatile memory for storing the sensed data, the period staff notation being entered into the non-volatile memory.

7. The ambulatory data recorder according to claim 1, wherein the means for sampling the sensed physiologic data comprises a pH sensing catheter.

8. The ambulatory data recorder according to claim 1, further comprising a means for mounting the ambulatory recorder to a patient.

9. The ambulatory data recorder according to claim 1, wherein the mounting means comprises a loop configured for a belt or a shoulder strap to be inserted therethrough.

10. An ambulatory recorder according to claim 1, further comprising a housing, the housing having a first marking adjacent the first position of the slide switch and a second marking adjacent the second position of the slide switch.

11. An ambulatory recorder according to claim 10, wherein the first marking indicates a first patient activity and the second marking indicates the absence of the first patient activity.

12. An ambulatory recorder according to claim 11, wherein the first activity is eating.

13. An ambulatory recorder according to claim 11, wherein the first activity is sleeping.

14. An ambulatory data recorder, comprising:
   a sensor to sense physiologic data;
   means for sampling and recording the sensed physiologic data;
   a patient activated period slide switch, the slide switch being moveable from a first position to a second position; and
   a housing, the housing having a first marking adjacent the first position of the slide switch and a second marking adjacent the second position of the slide switch.

15. An ambulatory recorder according to claim 14, wherein the first marking indicates a first patient activity and the second marking indicates the absence of the first patient activity.

16. An ambulatory recorder according to claim 15, wherein the first activity is smoking.

17. An ambulatory recorder according to claim 15, wherein the first activity is sleeping.

18. An ambulatory recorder according to claim 14, wherein the means for sampling and recording the sensed physiologic data further comprises means for entering a period start notation in the recorded data when the slide switch is moved to the first position.

19. An ambulatory recorder according to claim 18, wherein the means for sampling and recording the sensed physiologic data further comprises means for entering a period end notation in the recorded data when the slide switch is moved to the second position.

20. An ambulatory recorder according to claim 18, wherein the slide switch is biased to the first position until moved to the second position, at which time the slide switch is biased in the second position, until moved to the first position.

21. An ambulatory recorder according to claim 14, wherein the slide switch slides in a linear manner.

22. An ambulatory recorder according to claim 14, wherein the means for sampling and recording the sensed physiologic data comprises a non real time processor.

23. An ambulatory recorder according to claim 22, wherein the processor further comprises keyboard interrupt service routines, the processor further having executable software to permit the slide switch movement to access a keyboard interrupt service routine in the means for sampling and recording the sensed physiologic data and thereby insert a period start notation in the recorded data when the slide switch is moved to the first position.

24. The ambulatory data recorder according to claim 14, wherein the means for sampling and recording the sensed physiologic data further comprises a non-volatile memory for storing the sensed data, the period start notation being entered into the non-volatile memory.

25. The ambulatory data recorder according to claim 14, wherein the means for sampling the sensed physiologic data comprises a pH sensing catheter.

26. The ambulatory data recorder according to claim 14, further comprising a mounting for mounting the ambulatory recorder to a patient.

27. The ambulatory data recorder according to claim 26, wherein the mounting comprises a loop configured for a belt or a shoulder strap to be inserted therethrough.

28. An ambulatory data recorder, comprising:
   a sensor to sense physiologic data;

a processor for sampling the sensed physiologic data;

a non-volatile memory for storing the sensed data, the non-volatile memory coupled to the processor; and a patient activated period slide switch, the slide switch being moveable from a first position, where a period start notation is made in the recorded data, to a second position, where a period end notation is made in the recorded data.

29. An ambulatory recorder according to claim 28, wherein the slide switch is biased to the first position until moved to the second position, at which time the slide switch is biased in the second position until moved to the first position.

30. An ambulatory recorder according to claim 29, wherein the slide switch slides in a linear manner.

31. An ambulatory recorder according to claim 29, wherein the processor further comprises keyboard interrupt service routines, the processor further having executable software to permit the slide switch movement to access a keyboard interrupt service routine in the means for sampling and recording the sensed physiologic data and thereby insert a period start notation in the recorded data when the slide switch is moved to the first position.

32. The ambulatory data recorder according to claim 29, wherein the means for sampling the sensed physiologic data comprises a pH sensing catheter.

33. The ambulatory data recorder according to claim 29, further comprising a means for mounting the ambulatory recorder to a patient.

34. The ambulatory data recorder according to claim 33, wherein the mounting, means comprises a loop configured for a belt or a shoulder strap to be inserted therethrough.

35. An ambulatory recorder according to claim 29, further comprising a housing, the housing having a first marking adjacent the first position of the slide switch and a second marking adjacent the second position of the slide switch.

36. An ambulatory recorder according to claim 35, wherein the first marking indicates a first patient activity and the second marking indicates the absence of the first patient activity.

37. An ambulatory recorder according to claim 36, wherein the first activity is eating.

38. An ambulatory recorder according to claim 36, wherein the first activity is sleeping.

* * * * *

UNITED STATES PATENT AND TRADEMARK OFFICE
CERTIFICATE OF CORRECTION

PATENT NO.    : 6,141,574
DATED         : October 31, 2000
INVENTOR(S)   : Satherley et al.

It is certified that error appears in the above-identified patent and that said Letters Patent is hereby corrected as shown below:

Column 7,
Line 29, change "until removed" to -- until moved --.

Signed and Sealed this

Eighteenth Day of March, 2003

JAMES E. ROGAN
*Director of the United States Patent and Trademark Office*